(12) United States Patent
Rahman et al.

(10) Patent No.: US 7,678,528 B2
(45) Date of Patent: Mar. 16, 2010

(54) PHOTOACTIVE COMPOUNDS

(75) Inventors: M. Dalil Rahman, Flemington, NJ (US);
Munirathna Padmanaban, Bridgewater, NJ (US)

(73) Assignee: AZ Electronic Materials USA Corp., Somerville, NJ (US)

( * ) Notice: Subject to any disclaimer, the term of this patent is extended or adjusted under 35 U.S.C. 154(b) by 0 days.

(21) Appl. No.: 11/355,400

(22) Filed: Feb. 16, 2006

(65) Prior Publication Data

US 2007/0111138 A1    May 17, 2007

Related U.S. Application Data

(63) Continuation-in-part of application No. 11/280,842, filed on Nov. 16, 2005, now abandoned.

(51) Int. Cl.
*G03F 7/004* (2006.01)
*C07C 381/12* (2006.01)

(52) U.S. Cl. .............. 430/270.1; 568/77; 430/913; 430/914; 430/921; 430/925

(58) Field of Classification Search .......... 430/270.1, 430/311, 319, 401, 434, 435, 494, 913, 921, 430/914, 923, 925, 322, 326; 522/25; 568/77
See application file for complete search history.

(56) References Cited

U.S. PATENT DOCUMENTS

| | | | |
|---|---|---|---|
| 5,159,088 A | 10/1992 | Schwaim | 549/3 |
| 5,554,664 A | 9/1996 | Lamanna et al. | 522/25 |
| 5,874,616 A | 2/1999 | Howells et al. | 564/82 |
| 5,880,169 A * | 3/1999 | Osawa et al. | 522/25 |
| 6,010,820 A | 1/2000 | Aoai et al. | 430/270.1 |
| 6,051,370 A | 4/2000 | Kim | 430/326 |
| 6,100,198 A * | 8/2000 | Grieger et al. | 438/692 |
| 6,358,665 B1 | 3/2002 | Pawlowski et al. | 430/270.1 |
| 6,383,713 B1 | 5/2002 | Uetani et al. | 430/270.1 |
| 6,548,221 B2 | 4/2003 | Uetani et al. | 430/270.1 |
| 6,841,333 B2 | 1/2005 | Lamanna et al. | 430/270.1 |
| 6,855,476 B2 | 2/2005 | Ferreira et al. | 430/270.1 |
| 6,908,722 B2 | 6/2005 | Ebata et al. | 430/270.1 |
| 6,924,323 B2 | 8/2005 | Ishihara et al. | 522/25 |
| 6,991,888 B2 | 1/2006 | Padmanaban et al. | 430/270.1 |
| 7,078,444 B2 | 7/2006 | Lamanna et al. | 522/25 |
| 7,390,613 B1 | 6/2008 | Rahman et al. | 430/270.1 |
| 7,491,482 B2 | 2/2009 | Padmanaban et al. | 430/270.1 |
| 7,521,170 B2 | 4/2009 | Rahmna et al. | 430/270.1 |
| 2002/0197558 A1* | 12/2002 | Ferreira et al. | 430/270.1 |
| 2003/0113659 A1 | 6/2003 | Hatakeyama et al. | 430/270.1 |
| 2003/0148211 A1* | 8/2003 | Kamabuchi et al. | 430/270.1 |
| 2003/0235782 A1* | 12/2003 | Padmanaban et al. | 430/270.1 |
| 2004/0229155 A1 | 11/2004 | Rahman et al. | 430/270.1 |
| 2004/0234888 A1 | 11/2004 | Lamanna | 430/270.1 |
| 2005/0053861 A1* | 3/2005 | Yoneda et al. | 430/270.1 |
| 2005/0064340 A1* | 3/2005 | Aoai | 430/302 |

FOREIGN PATENT DOCUMENTS

| | | |
|---|---|---|
| DE | 295 421 A5 | 10/1983 |
| EP | 0 795 786 A | 9/1997 |
| EP | 0 795 786 A2 | 9/1998 |
| EP | 1020767 A1 * | 7/2000 |
| JP | 2000-275845 A | 10/2000 |
| JP | 2003-267949 A | 9/2003 |
| JP | 2004-359590 A | 12/2004 |
| JP | 2005-092053 | 4/2005 |
| JP | 2005-099456 | 4/2005 |
| JP | 2005-148291 | 6/2005 |
| JP | 2005-227645 | 8/2005 |
| JP | 2005-258124 | 9/2005 |
| JP | 3763239 B2 | 1/2006 |
| JP | 2007-178858 | 7/2007 |
| WO | WO 02/082185 | 10/2002 |
| WO | WO 2007/007175 A2 | 1/2007 |
| WO | WO 2007/007175 A3 | 1/2007 |
| WO | WO 2007/124092 | 11/2007 |

OTHER PUBLICATIONS

Notification Concerning Transmittal of International Preliminary Report on Patentability (Chapter I of the Patent Cooperation Treaty) (Form PCT/IB/326) for PCT/IB2006/001931, which corresponds to related U.S. Appl. No. 11/355,762.
International Preliminary Report on Patentability (Chapter I of the Patent Cooperation Treaty) (Form PCT/IB/373) for PCT/IB2006/001931, which corresponds to related U.S. Appl. No. 11/355,762.
Written Opinion of the Searching Authority (Form PCT/ISA/237) for PCT/IB2006/001931(attached to Form PCT/IB/326), which corresponds to related U.S. Appl. No. 11/355,762.
Office Action from U.S. Appl. No. 11/566,312, dated Mar. 26, 2008.
Notification Concerning Transmittal of International Preliminary Report on Patentability (Chapter I of the Patent Cooperation Treaty) (Form PCT/IB/326), International Preliminary Report on Patentability (Form PCT/IB/373), and Written Opinion of the International Searching Authority (Form PCT/ISA/237) for PCT/IB2006/003315 corresponding to the above application.
International Search Report for PCT/IB2007/003989.
Written Opinion of International Searching Authority for PCT/IB2007/003989.
Notification of Transmittal of the International Search Report and the Written Opinion of the International Searching Authority, or the Declaration for PCT/IB2007/003989.
English language abstract of JP 2005-099456 from European Patent Office.
English language abstract of JP 2005-092053 from European Patent Office.
International Search Report for PCT/IB2007/003823.
Written Opinion of International Searching Authority for PCT/IB2007/003823.
Notification of Transmittal of the International Search Report and the Written Opinion of the International Searching Authority, or the Declaration for corresponding PCT application PCT/IB2006/003315, Sep. 10, 2007.

(Continued)

*Primary Examiner*—Cynthia H Kelly
*Assistant Examiner*—Anca Eoff
(74) *Attorney, Agent, or Firm*—Sangya Jain; Alan P. Kase

(57) ABSTRACT

The present invention relates to novel photoacid generators.

9 Claims, No Drawings

OTHER PUBLICATIONS

International Search Report for corresponding PCT application PCT/IB2006/003315, Sep. 10, 2007.
Written Opinion of the International Searching Authority for corresponding PCT application PCT/IB2006/003315, Sep. 10, 2007.
English Language Abstract of JP 2004-359590 A, Dec. 24, 2004.
Invitation to Pay Additional Fees and International Search Report (Form PCT/ISA/206) for corresponding PCT application PCT/IB2006/003315, Jun. 11, 2007.
Invitation to Pay Additional Fees with partial International Search Report (Form PCT/ISA/206) for corresponding PCT application PCT/IB2006/001931 (PCT of U.S. Appl. No. 11/355,762), Nov. 17, 2006.
Notification of Transmittal of the International Search Report and the Written Opinion of the International Searching Authority, or the Declaration (Form PCT/ISA/220) for corresponding PCT application PCT/IB2006/001931 (PCT of U.S. Appl. No. 11/355,762), Jan. 26, 2007.
International Search Report (Form PCT/ISA/210) for corresponding PCT application PCT/IB2006/001931 (PCT of U.S. Appl. No. 11/355,762), Jan. 25, 2007.
Written Opinion of the International Searching Authority (Form PCT/ISA/237) for corresponding PCT application PCT/IB2006/001931 (PCT of U.S. Appl. No. 11/355,762), Jan. 25, 2007.
English Language Abstract of JP 2003-267949 A, Sep. 25, 2003.
Office Action dated Jun. 19, 2008 from related case U.S. Appl. No. 11/566,312.

* cited by examiner

PHOTOACTIVE COMPOUNDS

CROSS-REFERENCE TO RELATED APPLICATION

This application is a continuation-in-part application of Ser. No. 11/280,842, filed Nov. 16, 2005, now abandoned the contents of which are hereby incorporated herein by reference.

FIELD OF INVENTION

The present invention relates to novel photoactive compounds useful in photoresist compositions in the field of microlithography, and especially useful for imaging negative and positive patterns in the production of semiconductor devices, as well as photoresist compositions and processes for imaging photoresists.

BACKGROUND OF THE INVENTION

Photoresist compositions are used in microlithography processes for making miniaturized electronic components such as in the fabrication of computer chips and integrated circuits. Generally, in these processes, a thin coating of film of a photoresist composition is first applied to a substrate material, such as silicon wafers used for making integrated circuits. The coated substrate is then baked to evaporate any solvent in the photoresist composition and to fix the coating onto the substrate. The photoresist coated on the substrate is next subjected to an image-wise exposure to radiation.

The radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation exposed or the unexposed areas of the photoresist. The trend toward the miniaturization of semiconductor devices has led to the use of new photoresists that are sensitive at lower and lower wavelengths of radiation and has also led to the use of sophisticated multilevel systems to overcome difficulties associated with such miniaturization.

There are two types of photoresist compositions: negative-working and positive-working. The type of photoresist used at a particular point in lithographic processing is determined by the design of the semiconductor device. When negative-working photoresist compositions are exposed image-wise to radiation, the areas of the photoresist composition exposed to the radiation become less soluble to a developer solution (e.g. a cross-linking reaction occurs) while the unexposed areas of the photoresist coating remain relatively soluble to such a solution. Thus, treatment of an exposed negative-working resist with a developer causes removal of the non-exposed areas of the photoresist coating and the creation of a negative image in the coating, thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the creation of a positive image in the photoresist coating. Again, a desired portion of the underlying surface is uncovered.

Photoresist resolution is defined as the smallest feature, which the resist composition can transfer from the photomask to the substrate with a high degree of image edge acuity after exposure and development. In many leading edge manufacturing applications today, photoresist resolution on the order of less than one-half micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the push toward miniaturization reduces the critical dimensions on the devices. In cases where the photoresist dimensions have been reduced to below 150 nm, the roughness of the photoresist patterns has become a critical issue. Edge roughness, commonly known as line edge roughness, is typically observed for line and space patterns as roughness along the photoresist line, and for contact holes as side wall roughness. Edge roughness can have adverse effects on the lithographic performance of the photoresist, especially in reducing the critical dimension latitude and also in transferring the line edge roughness of the photoresist to the substrate. Hence, photoresists that minimize edge roughness are highly desirable.

Photoresists sensitive to short wavelengths, between about 100 nm and about 300 nm are often used where subhalfmicron geometries are required. Particularly preferred are photoresists comprising non-aromatic polymers, a photoacid generator, optionally a dissolution inhibitor, and solvent.

High resolution, chemically amplified, deep ultraviolet (100-300 nm) positive and negative tone photoresists are available for patterning images with less than quarter micron geometries. To date, there are three major deep ultraviolet (UV) exposure technologies that have provided significant advancement in miniaturization, and these use lasers that emit radiation at 248 nm, 193 nm and 157 nm. Photoresists used in the deep UV typically comprise a polymer which has an acid labile group and which can deprotect in the presence of an acid, a photoactive component which generates an acid upon absorption of light, and a solvent.

Photoresists for 248 nm have typically been based on substituted polyhydroxystyrene and its copolymers, such as those described in U.S. Pat No. 4,491,628 and U.S. Pat. No. 5,350,660. On the other hand, photoresists for 193 nm exposure require non-aromatic polymers, since aromatics are opaque at this wavelength. U.S. Pat. No. 5,843,624 and GB 2,320,718 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon: hydrogen ratios which improve etch resistance, they also provide transparency at low wavelengths and they have relatively high glass transition temperatures. Photoresists sensitive at 157 nm have been based on fluorinated polymers, which are known to be substantially transparent at that wavelength. Photoresists derived from polymers containing fluorinated groups are described in WO 00/67072 and WO 00/17712.

The polymers used in a photoresist are designed to be transparent to the imaging wavelength, but on the other hand, the photoactive component has been typically designed to be absorbing at the imaging wavelength to maximize photosensitivity. The photosensitivity of the photoresist is dependent on the absorption characteristics of the photoactive component, the higher the absorption, the less the energy required to generate the acid, and the more photosensitive is the photoresist.

SUMMARY OF THE INVENTION

The present invention relates to a compound having the formula

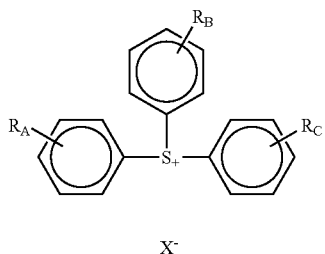

X⁻ where $R_A$, $R_B$, and $R_C$ are each independently hydrogen or $OR_1$, where each $R_1$ is independently hydrogen, alkyl, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, $SO_2R_4$, and $SiR_4$, where $R_4$ is alkyl, aryl, or monocycloalkyl or polycycloalkyl group with the cycloalkyl ring optionally containing one or more O atoms, the alkyl, alkoxyalkyl, alkoxycarbonylalkyl, alkylcarbonyl, aryl, monocycloalkyl- or polycycloalkyloxycarbonylalkyl with the cycloalkyl ring optionally containing one or more O atoms, monocycloalkyl- or polycycloalkyloxyalkly with the cycloalkyl ring containing one or more O atoms, and monocycloalkyl or polycycloalkyl group with the cycloalkyl ring containing one or more O atoms being unsubstituted or substituted by one or more of halogen, alkyl, monocycloalkyl or polycycloalkyl, alkoxy, cycloalkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

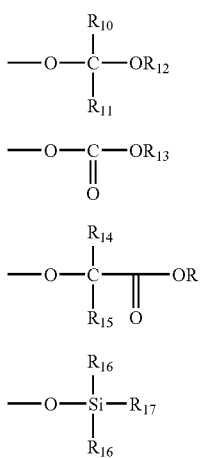

(II)

(III)

(IV)

(V)

-continued

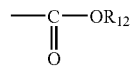

(VI)

wherein $R_{10}$ and $R_{11}$ each independently represent a hydrogen atom, a straight or branched alkyl chain optionally containing one or more O atoms, or a monocycloalkyl or polycycloalkyl group, or $R_{10}$ and $R_{11}$ together can represent an alkylene group to form a five- or six-membered ring, $R_{12}$ represents a straight or branched alkyl chain optionally containing one or more O atoms, a monocycloalkyl or polycycloalkyl group, or an aralkyl group, or $R_{10}$ and $R_{12}$ together represent an alkylene group which forms a five- or six-membered ring together with the interposing —C—O— group, the carbon atom in the ring being optionally substituted by an oxygen atom, $R_{13}$ represents a straight or branched alkyl chain optionally containing one or more O atoms or a monocycloalkyl or polycycloalkyl group, $R_{14}$ and $R_{15}$ each independently represent a hydrogen atom, a straight or branched alkyl chain optionally containing one or more O atoms or a monocycloalkyl or polycycloalkyl group, $R_{16}$ represents a straight or branched alkyl chain optionally containing one or more O atoms, a monocycloalkyl or polycycloalkyl group, aryl, or aralkyl, and $R_{17}$ represents $C_{1-20}$ straight or branched alkyl chain optionally containing one or more O atoms, a monocycloalkyl or polycycloalkyl group, aryl, aralkyl, the group —Si$(R_{16})_2$$R_{17}$, or the group —O—Si$(R_{16})_2R_{17}$, the $C_{1-20}$ straight or branched alkyl chain optionally containing one or more O atoms, monocycloalkyl or polycycloalkyl group, aryl, and aralkyl being unsubstituted or substituted as above; and X⁻ is an anion:

The present invention also relates to a photoresist composition useful for imaging in deep UV comprising a polymer containing an acid labile group and a compound of the present invention. The present invention also relates to a process for imaging a photoresist comprising the steps of coating a substrate with the composition of the present invention, baking the substrate to substantially remove the solvent, image-wise exposing the photoresist coating, postexposure baking the photoresist coating, and developing the photoresist coating with an aqueous alkaline solution.

DETAILED DESCRIPTION OF THE INVENTION

The present invention relates to a compound having the formula

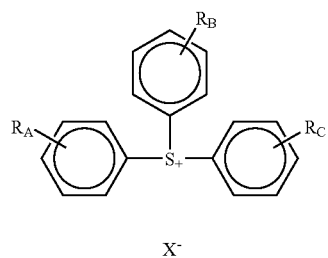

X⁻ where $R_A$, $R_B$, and $R_C$ are each independently hydrogen or $OR_1$, where each $R_1$ is independently hydrogen, alkyl, alkoxyalkyl, alkoxycarbonylalkyl, alkylcarbonyl, monocycloalkyl- or polycycloalkyloxycarbonylalkyl with the cycloalkyl ring optionally containing one or more O atoms, monocycloalkyl- or polycycloalkyloxyalkyl with the cycloalkyl ring optionally containing one or more O atoms, $SO_2R_4$, and $SiR_4$, where $R_4$ is alkyl, aryl, or monocycloalkyl or polycycloalkyl group with the cycloalkyl ring optionally containing one or more O atoms, the alkyl, alkoxyalkyl, alkoxycarbonylalkyl, alkylcarbonyl, aryl, monocycloalkyl- or polycycloalkyloxycarbonylalkyl with the cycloalkyl ring optionally containing one or more O atoms, monocycloalkyl- or polycycloalkyloxyalkly with the cycloalkyl ring containing one or more O atoms, and monocycloalkyl or polycycloalkyl group with the cycloalkyl ring containing one or more O atoms being unsubstituted or substituted by one or more of halogen, alkyl, monocycloalkyl or polycycloalkyl, alkoxy, cycloalkoxy, dialkylamino, dicyclic dialkylamino, hydroxyl, cyano, nitro, tresyl, oxo, aryl, aralkyl, oxygen atom, $CF_3SO_3$, aryloxy, arylthio, and groups of formulae (II) to (VI):

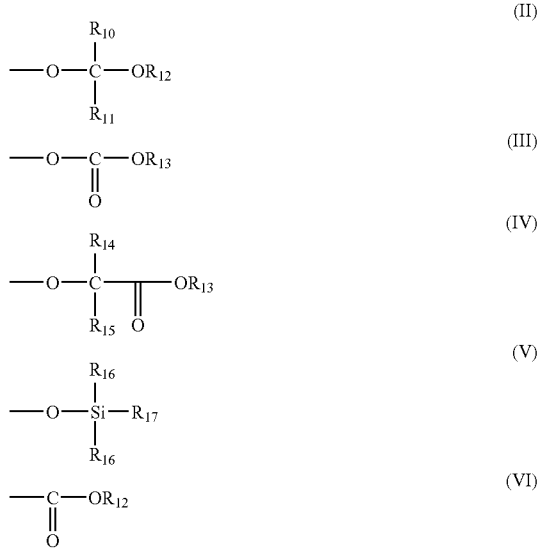

wherein $R_{10}$ and $R_{11}$ each independently represent a hydrogen atom, a straight or branched alkyl chain optionally containing one or more O atoms, or a monocycloalkyl or polycycloalkyl group, or $R_{10}$ and $R_{11}$ together can represent an alkylene group to form a five- or six-membered ring, $R_{12}$ represents a straight or branched alkyl chain optionally containing one or more O atoms, a monocycloalkyl or polycycloalkyl group, or aralkyl, or $R_{10}$ and $R_{12}$ together represent an alkylene group which forms a five- or six-membered ring together with the interposing —C—O— group, the carbon atom in the ring being optionally substituted by an oxygen atom, $R_{13}$ represents a straight or branched alkyl chain optionally containing one or more O atoms or a monocycloalkyl or polycycloalkyl group, $R_{14}$ and $R_{15}$ each independently represent a hydrogen atom, a straight or branched alkyl chain optionally containing one or more O atoms or a monocycloalkyl or polycycloalkyl group, $R_{16}$ represents a straight or branched alkyl chain optionally containing one or more O atoms, a monocycloalkyl or polycycloalkyl group, aryl, or aralkyl, and $R_{17}$ represents $C_{1-20}$ straight or branched alkyl chain optionally containing one or more O atoms, a monocycloalkyl or polycycloalkyl group, aryl, aralkyl, the group —Si($R_{16}$)$_2$ $R_{17}$, or the group —O—Si($R_{16}$)$_2R_{17}$, the $C_{1-20}$ straight or branched alkyl chain optionally containing one or more O atoms, monocycloalkyl or polycycloalkyl group, aryl, and aralkyl being unsubstituted or substituted as above; and $X^-$ is an anion.

The present invention also relates to a photoresist composition useful for imaging in deep UV comprising a polymer containing an acid labile group and a compound of the present invention. The present invention also relates to a process for imaging a photoresist comprising the steps of coating a substrate with the composition of the present invention, baking the substrate to substantially remove the solvent, image-wise exposing the photoresist coating, postexposure baking the photoresist coating, and developing the photoresist coating with an aqueous alkaline solution.

The term alkyl as used herein means a straight or branched chain hydrocarbon. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

Alkylene refers to divalent alkyl radicals, which can be linear or branched, such as, for example, methylene, ethylene, propylene, butylene or the like.

Carbonyl refers to —C(O)—.

The term monocycloalkyl, as used herein, refers to an optionally substituted, saturated or partially unsaturated monocycloalkyl ring system, where if the ring is partially unsaturated, it is then a monocycloalkenyl group. Examples of such monocycloalkyl rings include cyclopropyl, cyclobutyl, cyclopentyl, cyclohexyl or cycloheptyl.

The term polycycloalkyl as used herein refers to an optionally substituted saturated or partially unsaturated polycycloalkyl ring system containing two or more rings, where if the ring system is partially unsaturated, it is then a polycycloalkenyl group. Examples of such polycycloalkyl rings include, but are not limited to, 3-oxatricyclo[4.2.1.0$^{2,5}$]nonyl, tetracyclo[5.2.2.0.0]undecanyl, bornyl, isobornyl, norbornyl, and adamantyl.

The term aryl as used herein refers to a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthryl, phenanthryl, and the like.

The term alkenyl as used herein, refers to a group derived from a straight or branched chain hydrocarbon containing at least one double bond.

The term alkoxy refers to a group of alkyl-O—, where alkyl is defined herein. Representative examples of alkoxy include, but are not limited to, methoxy, ethoxy, propoxy, 2-propoxy, butoxy, tert-butoxy, pentyloxy, and hexyloxy.

The term aryloxy refers to a group of aryl-O—, where aryl is defined herein.

The term alkoxycarbonylalkyl embraces alkyl radicals substituted with an alkoxycarbonyl radical as defined herein. Examples of alkoxycarbonylalkyl radicals include methoxycarbonylmethyl [$CH_3O$—C(=O)—$CH_2$—], ethoxycarbonylmethyl [CH$_3$CH$_2$O—C(=O)CH$_2$—], methoxycarbonylethyl [CH$_3$O—C(=O)—CH$_2$CH$_2$—], and ethoxycarbonylethyl [CH$_3$CH$_2$O—C(=O)—CH$_2$CH$_2$—].

The term cycloalkoxy refers to a group of monocycloalkyl—O— or polycycloalkyl-O—, where monocycloalkyl or polycycloalkyl is defined herein.

The term alkylcarbonyl as used herein means an alkyl group, as defined herein, appended to the parent molecular moiety through a carbonyl group, as defined herein, which can be generically represented as alkyl-C(O)—. Representative examples of alkylcarbonyl include, but are not limited to acetyl (methyl carbonyl), butyryl (propylcarbonyl), octanoyl (heptylcarbonyl), dodecanoyl (undecylcarbonyl), and the like.

Alkoxycarbonyl means alkyl-O—C(O)—, wherein alkyl is as previously described. Non-limiting examples include methoxycarbonyl [CH$_3$O—C(O)—] and the ethoxycarbonyl [CH$_3$CH$_2$O—C(O)—], benzyloxycarbonyl [C$_6$H$_5$CH$_2$O—C(O)—] and the like.

Alkoxyalkyl means that a terminal alkyl group is linked through an ether oxygen atom to an alkyl moiety, which can be generically represented as alkyl-O— alkyl wherein the alkyl groups can be linear or branched. Examples of alkoxyalkyl include, but are not limited to, methoxypropyl, methoxybutyl, ethoxypropyl, methoxymethyl Monocycloalkyl- or polycycloalkyloxycarbonylalkyl means that a terminal monocycloalkyl or polycycloalkyl group is linked through —O—C(=O)— to an alkyl moiety, generically represented as monocycloalkyl- or polycycloalky-O—C(=O)-alkyl.

Monocycloalkyl- or polycycloalkyloxyalkyl means that a terminal monocycloalkyl or polycycloalkyl group is linked through an ether oxygen atom to an alkyl moiety, which can be generically represented as monocycloalkyl- or polycycloalkyl-O-alkyl.

The term aralkyl refers to an alkyl group in which one hydrogen atom is replaced by an aryl group, wherein aryl and alkyl are as defined above. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, naphthylmethyl, and the like.

Examples of X$^-$, the anion, include those commonly found with photoacid generators and can include, for example, CF$_3$SO$_3^-$, CHF$_2$SO$_3^-$, CH$_3$SO$_3^-$, CCl$_3$SO$_3^-$, C$_2$F$_5$SO$_3^-$, C$_2$HF$_4$SO$_3^-$, C$_4$F$_9$SO$_3^-$, pentafluorobenzene sulfonate, (Rf1SO$_2$)$_3$C$^-$ and (Rf1SO$_2$)$_2$N$^-$, wherein each Rf1 is independently selected from the group consisting of highly fluorinated or perfluorinated alkyl or fluorinated aryl radicals and may be cyclic, when a combination of any two Rf1 groups are linked to form a bridge, further, the Rf1 alkyl chains contain from 1-20 carbon atoms optionally containing a catenary oxygen and may be straight, branched, or cyclic, such that divalent oxygen, trivalent nitrogen or hexavalent sulfur may interrupt the skeletal chain, further when Rf1 contains a cyclic structure, such structure has 5 or 6 ring members, optionally, 1 or 2 of which are heteroatoms, and Rg-O—Rf2-SO$_3^-$, where Rf2 is selected from the group consisting of linear or branched (CF$_2$)$_j$ where j is an integer from 4 to 10 and C$_1$-C$_{12}$ perfluorocycloalkyl divalent radical which is optionally perfluoro C$_{1-10}$alkyl substituted, Rg is selected from the group consisting of C$_1$-C$_{20}$ linear, branched, monocycloalkyl or polycycloalkyl, C$_1$-C$_{20}$ linear, branched, monocycloalkenyl or polycycloalkenyl, aryl, and aralkyl, the alkyl, alkenyl, aralkyl and aryl groups being unsubstituted, substituted, optionally containing one or more catenary oxygen atoms, partially fluorinated or perfluorinated. Examples include (C$_2$F$_5$SO$_2$)$_2$N$^-$, (C$_4$F$_9$SO$_2$)$_2$N$^-$, (C$_8$F$_{17}$SO$_2$)$_3$C$^-$, (CF$_3$SO$_2$)$_3$C$^-$, (CF$_3$SO$_2$)$_2$N$^-$, (SO$_2$C$_8$F$_{17}$)$_2$N$^-$, (SO$_2$CF$_3$)(SO$_2$C$_8$F$_{17}$)N$^-$, (CF$_3$SO$_2$)(C$_4$F$_9$SO$_2$)N$^-$, (SO$_2$C$_3$F$_7$)$_2$N$^-$, (C$_2$F$_5$SO$_2$)$_3$C$^-$, (C$_4$F$_9$SO$_2$)$_3$C$^-$, (CF$_3$SO$_2$)$_2$(C$_2$F$_5$SO$_2$)C$^-$, (C$_4$F$_9$SO$_2$)(C$_2$F$_5$SO$_2$)$_2$C$^-$, (CF$_3$SO$_2$)(C$_4$F$_9$SO$_2$)N$^-$, [(CF$_3$)$_2$NC$_2$F$_4$SO$_2$]$_2$N$^-$, (CF$_3$)$_2$NC$_2$F$_4$SO$_2$C$^-$(SO$_2$CF$_3$)$_2$, (3,5-bis (CF$_3$)C$_6$H$_3$)SO$_2$N$^-$SO$_2$CF$_3$, C$_6$F$_5$SO$_2$C$^-$(SO$_2$CF$_3$)$_2$, C$_6$F$_5$SO$_2$N$^-$SO$_2$CF$_3$,

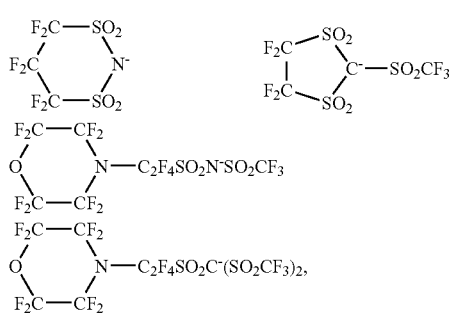

CF$_3$CHFO(CF$_2$)$_4$SO$_3^-$, CF$_3$CH$_2$O(CF$_2$)$_4$SO$_3^-$, CH$_3$CH$_2$O(CF$_2$)$_4$SO$_3^-$, CH$_3$CH$_2$CH$_2$O(CF$_2$)$_4$SO$_3^-$, CH$_3$O(CF$_2$)$_4$SO$_3^-$, C$_2$H$_5$O(CF$_2$)$_4$SO$_3^-$, C$_4$H$_9$O(CF$_2$)$_4$SO$_3^-$, C$_6$H$_5$CH$_2$O(CF$_2$)$_4$SO$_3^-$, C$_2$H$_5$OCF$_2$CF(CF$_3$)SO$^-$, CH$_2$=CHCH$_2$O(CF$_2$)$_4$SO$_3^-$, CH$_3$OCF$_2$CF(CF$_3$)SO$_3^-$, C$_4$H$_9$OCF$_2$CF(CF$_3$)SO$_3^-$, C$_8$H$_{17}$O(CF$_2$)$_2$SO$_3^-$, and C$_4$H$_9$O(CF$_2$)$_2$SO$_3^-$. Other examples of suitable anions can be found in U.S. Pat. No. 6,841,333 and U.S. Pat. No. 5,874,616.

Polymers useful in the photoresist compositions include those that have acid labile groups that make the polymer insoluble in aqueous alkaline solution, but such a polymer in the presence of an acid catalytically deprotects the polymer, wherein the polymer then becomes soluble in an aqueous alkaline solution. The polymers preferably are transparent below 200 nm, and are essentially non-aromatic, and preferably are acrylates and/or cycloolefin polymers. Such polymers are, for example, but not limited to, those described in U.S. Pat. No. 5,843,624, U.S. Pat. No. 5,879,857, WO 97/33, 198, EP 789,278 and GB 2,332,679. Nonaromatic polymers that are preferred for irradiation below 200 nm are substituted acrylates, cycloolefins, substituted polyethylenes, etc. Aromatic polymers based on polyhydroxystyrene and its copolymers may also be used, especially for 248 nm exposure.

Polymers based on acrylates are generally based on poly (meth)acrylates with at least one unit containing pendant alicyclic groups, and with the acid labile group being pendant from the polymer backbone and/or from the alicyclic group. Examples of pendant alicyclic groups, may be adamantyl, tricyclodecyl, isobornyl, menthyl and their derivatives. Other pendant groups may also be incorporated into the polymer, such as mevalonic lactone, gamma butyrolactone, alkyloxyalkyl, etc. Examples of structures for the alicyclic group include:

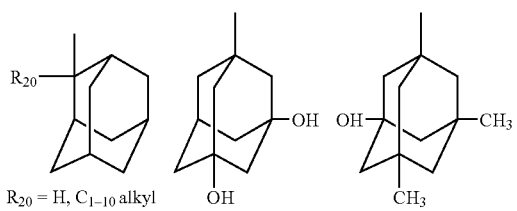
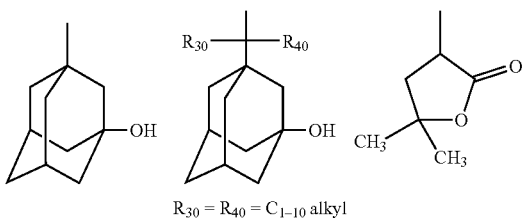
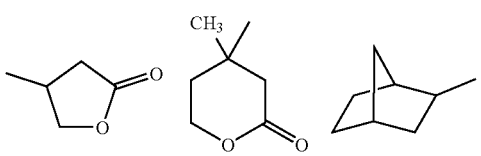
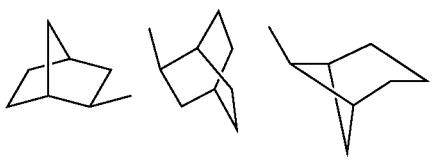
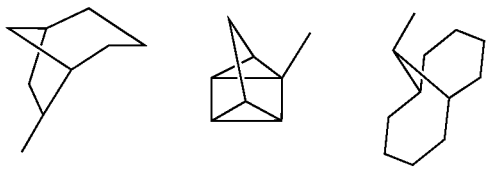
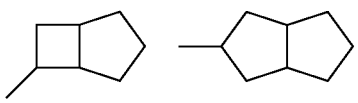
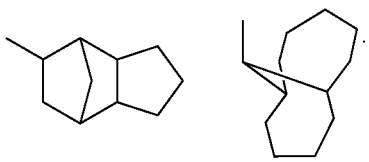

The type of monomers and their ratios incorporated into the polymer are optimized to give the best lithographic performance. Such polymers are described in R. R. Dammel et al., Advances in Resist Technology and Processing, SPIE, Vol. 3333, p 144, (1998). Examples of these polymers include poly(2-methyl-2-adamantyl methacrylate-co-mevalonic lactone methacrylate), poly(carboxy-tetracyclododecylmethacrylate-co-tetrahydropyranyl-carboxytetracyclododecylmethacrylate), poly(tricyclodecylacrylate-co-tetrahydropyranylmethacrylate-co-methacrylic acid), and poly(3-oxocyclohexyl methacrylate-co-adamantylmethacrylate).

Polymers synthesized from cycloolefins, with norbornene and tetracyclododecene derivatives, may be polymerized by ring-opening metathesis, free-radical polymerization or using metal organic catalysts. Cycloolefin derivatives may also be copolymerized with cyclic anhydrides or with maleimide or its derivatives. Examples of cyclic anhydrides are maleic anhydride (MA) and itaconic anhydride. The cycloolefin is incorporated into the backbone of the polymer and may be any substituted or unsubstituted multicyclic hydrocarbon containing an unsaturated bond. The monomer can have acid labile groups attached. The polymer may be synthesized from one or more cycloolefin monomers having an unsaturated bond. The cycloolefin monomers may be substituted or unsubstituted norbornene, or tetracyclododecane. The substituents on the cycloolefin may be aliphatic or cycloaliphatic alkyls, esters, acids, hydroxyl, nitrile or alkyl derivatives. Examples of cycloolefin monomers, without limitation, include:

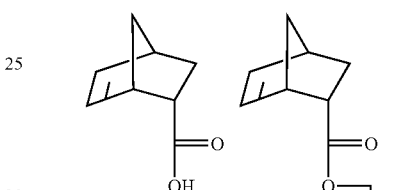
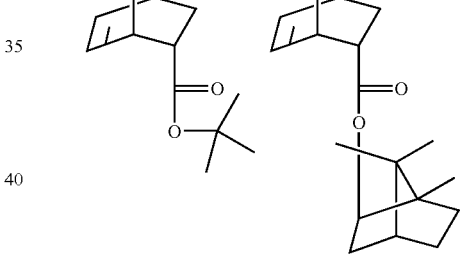
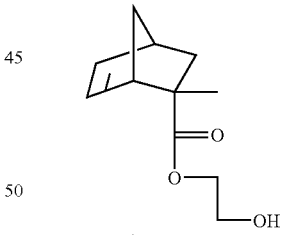
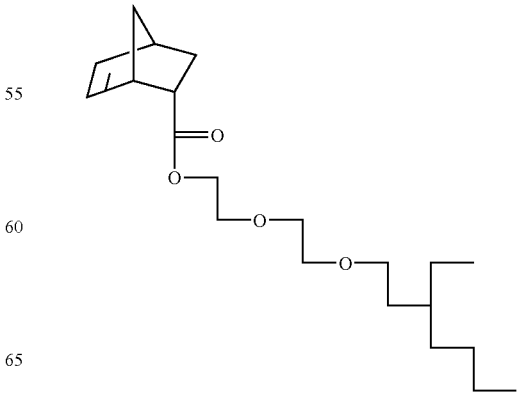

-continued

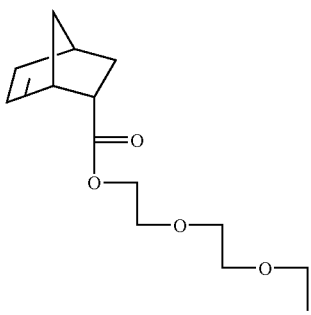

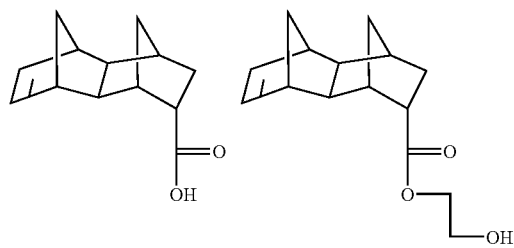

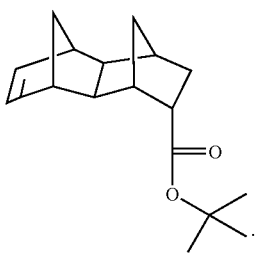

Other cycloolefin monomers which may also be used in synthesizing the polymer are:

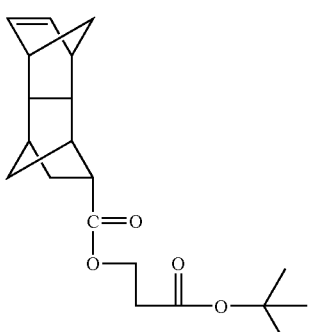

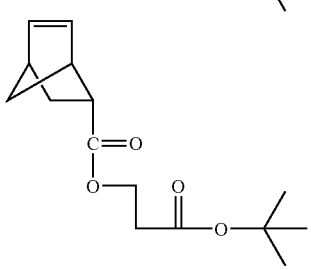

-continued

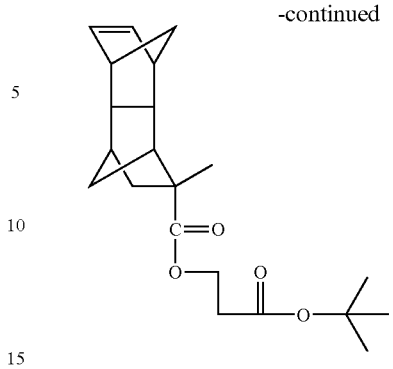

Such polymers are described in the following reference and incorporated herein, M-D. Rahman et al, Advances in Resist Technology and Processing, SPIE, Vol. 3678, p 1193, (1999). Examples of these polymers include poly((t-butyl 5-norbornene-2-carboxylate-co-2-hydroxyethyl 5-norbornene-2-carboxylate-co-5-norbornene-2-carboxylic acid-co-maleic anhydride), poly(t-butyl 5-norbornene-2-carboxylate-co-isobornyl-5-norbornene-2-carboxylate-co-2-hydroxyethyl 5-norbornene-2-carboxylate-co-5-norbornene-2-carboxylic acid-co-maleic anhydride), poly(tetracyclododecene-5-carboxylate-co-maleic anhydride), poly(t-butyl 5-norbornene-2-carboxylate-co-maleic anhydride-co-2-methyladamantyl methacrylate-co-2-mevalonic lactone methacrylate), poly(2-methyladamantyl methacrylate-co-2-mevalonic lactone methacylate) and the like.

Polymers containing mixtures of (meth)acrylate monomers, cycloolefinic monomers and cyclic anhydrides, where such monomers are described above, may also be combined into a hybrid polymer. Examples of cycloolefin monomers include those selected from t-butyl norbornene carboxylate (BNC), hydroxyethyl norbornene carboxylate (HNC), norbornene carboxylic acid (NC), t-butyltetracyclo[$4.4.0.1^{2,6}1^{7,10}$]dodec-8-ene-3-carboxylate, and t-butoxy carbonylmethyl tetracyclo[$4.4.0.1^{2,6}1^{7,10}$] dodec-8-ene-3-carboxylate. In some instances, preferred examples of cycloolefins include t-butyl norbornene carboxylate (BNC), hydroxyethyl norbornene carboxylate (HNC), and norbornene carboxylic acid (NC). Examples of (meth)acrylate monomers include those selected from mevalonic lactone methacrylate (MLMA), 2-methyl-2-adamantyl methacrylate (MAdMA), 2-adamantyl methacrylate (AdMA), 2-methyl-2-adamantyl acrylate (MAdA), 2-ethyl-2-adamantyl methacrylate (EAdMA), 3,5-dimethyl-7-hydroxy adamantyl methacrylate (DMHAdMA), isoadamantyl methacrylate, hydroxy-1-methacryloxyadamantane (HAdMA; for example, hydroxy at the 3-position), hydroxy-1-adamantyl acrylate (HADA; for example, hydroxy at the 3-position), ethylcyclopentylacrylate (ECPA), ethylcyclopentylmethacrylate (ECPMA), tricyclo[$5,2,1,0^{2,6}$]deca-8-yl methacrylate (TCDMA), 3,5-dihydroxy-1-methacryloxyadamantane (DHAdMA), β-methacryloxy-γ-butyrolactone, α- or β-gamma-butyrolactone methacrylate (either α- or β-GBLMA), 5-methacryloyloxy-2,6-norbornanecarbolactone (MNBL), 5-acryloyloxy-2,6-norbornanecarbolactone (ANBL), isobutyl methacrylate (IBMA), α-gamma-butyrolactone acrylate (α-GBLA), 2-adamantyl acrylate (AdA), norbornene lactone acrylate (NLA), spirolactone (meth)acrylate, oxytricyclodecane (meth)acrylate, adamantane lactone (meth)acrylate, and α-methacryloxy-γ-butyrolactone, among others. Examples of polymers formed with these monomers include poly(2-methyl-2-adamantyl methacrylate-co-2- ethyl-2-adamantyl methacrylate-co-3-hydroxy-1-methacryloxyadamantane-co-α-gamma-butyrolactone methacrylate); poly(2-ethyl-2-adamantyl methacrylate-co-3-hydroxy-1-methacryloxy-adamantane-co-β-gamma-butyrolactone methacrylate); poly(2-methyl-2-adamantyl methacrylate-co-3-hydroxy-1-methacryloxyadamantane-co-β-gamma-butyrolactone methacrylate); poly(t-butyl norbornene carboxylate-co-maleic anhydride-co-2-methyl-2-adamantyl methacrylate-co-β-gamma-butyrolactone methacrylate-co-methacryloyloxy norbornene methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-β-gamma-butyrolactone methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-methyl-2-adamantyl methacrylate-co-3,5-dihydroxy-1-methacryloxyadamantane-co-α-gamma-butyrolactone methacrylate); poly(2-methyl-2-adamantyl methacrylate-co-3,5-dimethyl-7-hydroxy adamantyl methacrylate-co-α-gamma-butyrolactone methacrylate); poly(2-methyl-2-adamantyl acrylate-co-3-hydroxy-1-methacryloxyadamantane-co-α-gamma-butyrolactone methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-methyl-2-adamantyl methacrylate-co-β-gamma-butyrolactone methacrylate-co-3-hydroxy-1-methacryloxyadamantane-co-ethylcyclopentylacrylate); poly(2-methyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-methacryloxyadamantane-co-α-gamma-butyrolactone methacrylate-co-2-ethyl-2-adamantyl methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$] deca-8-yl methacrylate); poly(2-methyl-2-adamantyl methacrylate-co-2-ethyl-2-adamantyl methacrylate-co-β-gamma-butyrolactone methacrylate-co-3-hydroxy-1-methacryloxy-adamantane); poly(2-methyl-2-adamantyl methacrylate-co-2-ethyl-2-adamantyl methacrylate-co-α-gamma-butyrolactone methacrylate-co-3-hydroxy-1-methacryloxyadamantane); poly(2-methyl-2-adamantyl methacrylate-co-methacryloyloxy norbornene methacrylate-co-β-gamma-butyrolactone methacrylate); poly(ethylcyclopentylmethacrylate-co-2-ethyl-2-adamantyl methacrylate-co-α-gamma-butyrolactone acrylate); poly(2-ethyl-2-adamantyl methacrylate-co-3-hydroxy-1-adamantyl acrylate-co-isobutyl methacrylate-co-α-gamma-butyrolactone acrylate); poly(2-methyl-2-adamantyl methacrylate-co-β-gamma-butyrolactone methacrylate-co-3-hydroxy-1-adamantyl acrylate-co-tricyclo[5,2,1,02,6]deca-8-yl methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-βgamma-butyrolactone methacrylate-co-2-adamantyl methacrylate-co-3-hydroxy-1-methacryloxy-adamantane); poly(2-methyl-2-adamantyl methacrylate-co-methacryloyloxy norbornene methacrylate-co-β-gamma-butyrolactone methacrylate); poly(2-methyl-2-adamantyl methacrylate-co-methacryloyloxy norbornene methacrylate-co-tricyclo[5,2,1,02,6]deca-8-yl methacrylate-co-3-hydroxy-1-methacryloxy-adamantane-co-α-gamma-butyrolactone methacrylate); poly(2-ethyl-2-adamantyl methacrylate-co-3-hydroxy-1-adamantyl acrylate-co-tricyclo[5,2,1,02,6]deca-8-yl methacrylate-co-α-gamma-butyrolactone methacrylate); poly(2-ethyl-2-adamantyl methacrylate-co-3-hydroxy-1-adamantyl acrylate-co-α-gamma-butyrolactone acrylate); poly(2-methyl-2-adamantyl methacrylate-co-3-hydroxy-1-methacryloxy-adamantane-co-α-gamma-butyrolactone methacrylate-co-2-ethyl-2-adamantyl-co-methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-adamantyl acrylate-co-5-acryloyloxy-2,6-norbornanecarbolactone); poly(2-ethyl-2-adamantyl methacrylate-co-3-hydroxy-1-adamantyl acrylate-co-α-gamma-butyrolactone methacrylate-co-α-gamma-butyrolactone acrylate); poly(2-ethyl-2-adamantyl methacrylate-co-3-hydroxy-1-adamantyl acrylate-co-α-gamma-butyrolactone methacrylate-co-2-adamantyl methacrylate); poly(2-ethyl-2-adamantylmethacrylate-co-3-hydroxy-1-adamantylacrylate-co-norbornenelactoneacrylate-co-2-sdamantylmethacrylate); poly(2-ethyl-2-adamantylmethacrylate-co-3-hydroxy-1-adamantylacrylate-co-norbornenelactoneacrylate-co-2-adamantylacrylate); and poly(2-ethyl-2-adamantyl methacrylate-co-3-hydroxy-1-adamantyl acrylate-co-α-gamma-butyrolactone acrylate-co-tricyclo[5,2,1,02,6]deca-8-yl methacrylate).

Other examples of suitable polymers include those described in U.S. Pat. Nos. 6,610,465, 6,120,977, 6,136,504, 6,013,416, 5,985,522, 5,843,624, 5,693,453, 4,491,628, WO 00/25178, WO 00/67072, JP 2000-275845, JP 2000-137327, and JP 09-73173 which are incorporated herein by reference. Blends of one or more photoresist resins may be used. Standard synthetic methods are typically employed to make the various types of suitable polymers. Procedures or references to suitable standard procedures (e.g., free radical polymerization) can be found in the aforementioned documents.

The cycloolefin and the cyclic anhydride monomer are believed to form an alternating polymeric structure, and the amount of the (meth)acrylate monomer incorporated into the polymer can be varied to give the optimal lithographic properties. The percentage of the (meth)acrylate monomer relative to the cycloolefin/anhydride monomers within the polymer ranges from about 95 mole % to about 5 mole %, further ranging from about 75 mole % to about 25 mole %, and also further ranging from about 55 mole % to about 45 mole %.

Fluorinated non-phenolic polymers, useful for 157 nm exposure, also exhibit line edge roughness and can benefit from the use of the novel mixture of photoactive compounds described in the present invention. Such polymers are described in WO 00/17712 and WO 00/67072 and incorporated herein by reference. Example of one such polymer is poly(tetrafluoroethylene-co-norbornene-co-5-hexafluoroisopropanol-substituted 2-norbornene.

Polymers synthesized from cycloolefins and cyano containing ethylenic monomers are described in the U.S. Pat. No. 6,686,429, the contents of which are hereby incorporated herein by reference, may also be used. Other polymers of interest include those found and described in U.S. patent application Ser. No. 10/371,262, filed Feb. 21, 2003, now filed as U.S. patent application Ser. No. 10/658,840, filed Dec. 17, 2003 (and published now as U.S. patent application publication no. 2004/0166433, the contents of which are incorporated herein by reference). Still other polymers, such as those disclosed in U.S. patent application Ser. No. 10/440,542, filed May 16, 2003 titled Photoresist Composition for Deep UV and Process Thereof, the contents of which are hereby incorporated herein by reference, may also be used.

The molecular weight of the polymers is optimized based on the type of chemistry used and on the lithographic performance desired. Typically, the weight average molecular weight is in the range of 3,000 to 30,000 and the polydispersity is in the range 1.1 to 5, preferably 1.5 to 2.5.

When the photoacid generators of the present invention are used in compositions, the solid components thereof are dissolved in an organic solvent. The amount of solids in the solvent or mixture of solvents ranges from about 1 weight % to about 50 weight %. The polymer may be in the range of 5 weight % to 90 weight % of the solids and the photoacid generator may be in the range of 1 weight % to about 50 weight % of the solids. Suitable solvents for such photoresists may include for example ketones such as acetone, methyl ethyl ketone, methyl isobutyl ketone, cyclohexanone, isophorone, methyl isoamyl ketone, 2-heptanone 4-hydroxy, and 4-methyl 2-pentanone; $C_1$ to $C_{10}$ aliphatic alcohols such as methanol, ethanol, and propanol; aromatic group containing-alcohols such as benzyl alcohol; cyclic carbonates such as ethylene carbonate and propylene carbonate; aliphatic or aromatic hydrocarbons (for example, hexane, toluene, xylene, etc and the like); cyclic ethers, such as dioxane and tetrahydrofuran; ethylene glycol; propylene glycol; hexylene glycol; ethylene glycol monoalkylethers such as ethylene glycol monomethylether, ethylene glycol monoethylether; ethylene glycol alkylether acetates such as methylcellosolve acetate and ethylcellosolve acetate; ethylene glycol dialkylethers such as ethylene glycol dimethylether, ethylene glycol diethylether, ethylene glycol methylethylether, diethylene glycol monoalkylethers such as diethylene glycol monomethylether, diethylene glycol monoethylether, and diethylene glycol dimethylether; propylene glycol monoalkylethers such as propylene glycol methylether, propylene glycol ethylether, propylene glycol propylether, and propylene glycol butylether; propylene glycol alkyletheracetates such as propylene glycol methylether acetate, propylene glycol ethylether acetate, propylene glycol propylether acetate, and propylene glycol butylether acetate; propylene glycol alkyletherpropionates such as propylene glycol methyletherpropionate, propylene glycol ethyletherpropionate, propylene glycol propyletherpropionate, and propylene glycol butyletherpropionate; 2-methoxyethyl ether (diglyme); solvents that have both ether and hydroxy moieties such as methoxy butanol, ethoxy butanol, methoxy propanol, and ethoxy propanol; esters such as methyl acetate, ethyl acetate, propyl acetate, and butyl acetate methyl-pyruvate, ethyl pyruvate; ethyl 2-hydroxy propionate, methyl 2-hydroxy 2-methyl propionate, ethyl 2-hydroxy 2-methyl propionate, methyl hydroxy acetate, ethyl hydroxy acetate, butyl hydroxy acetate, methyl lactate, ethyl lactate, propyl lactate, butyl lactate, methyl 3-hydroxy propionate, ethyl 3-hydroxy propionate, propyl 3-hydroxy propionate, butyl 3-hydroxy propionate, methyl 2-hydroxy 3-methyl butanoic acid, methyl methoxy acetate, ethyl methoxy acetate, propyl methoxy acetate, butyl methoxy acetate, methyl ethoxy acetate, ethyl ethoxy acetate, propyl ethoxy acetate, butyl ethoxy acetate, methyl propoxy acetate, ethyl propoxy acetate, propyl propoxy acetate, butyl propoxy acetate, methyl butoxy acetate, ethyl butoxy acetate, propyl butoxy acetate, butyl butoxy acetate, methyl 2-methoxy propionate, ethyl 2-methoxy propionate, propyl 2-methoxy propionate, butyl 2-methoxy propionate, methyl 2-ethoxypropionate, ethyl 2-ethoxypropionate, propyl 2-ethoxypropionate, butyl 2-ethoxypropionate, methyl 2-butoxypropionate, ethyl 2-butoxypropionate, propyl 2-butoxypropionate, butyl 2-butoxypropionate, methyl 3-methoxypropionate, ethyl 3-methoxypropionate, propyl 3-methoxypropionate, butyl 3-methoxypropionate, methyl 3-ethoxypropionate, ethyl 3-ethoxypropionate, propyl 3-ethoxypropionate, butyl 3-ethoxypropionate, methyl 3-propoxypropionate, ethyl 3-propoxypropionate, propyl 3-propoxypropionate, butyl 3-propoxypropionate, methyl 3-butoxypropionate, ethyl 3-butoxypropionate, propyl 3-butoxypropionate, and butyl 3-butoxypropionate; oxyisobutyric acid esters, for example, methyl-2-hydroxyisobutyrate, methyl α-methoxyisobutyrate, ethyl methoxyisobutyrate, methyl a-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate; solvents that have both ether and hydroxy moieties such as methoxy butanol, ethoxy butanol, methoxy propanol, and ethoxy propanol; and other solvents such as dibasic esters, and gamma-butyrolactone.; a ketone ether derivative such as diacetone alcohol methyl ether; a ketone alcohol derivative such as acetol or diacetone alcohol; lactones such as butyrolactone; an amide derivative such as dimethylacetamide or dimethylformamide, anisole, and mixtures thereof.

Various other additives such as colorants, non-actinic dyes, anti-striation agents, plasticizers, adhesion promoters, dissolution inhibitors, coating aids, photospeed enhancers, additional photoacid generators, and solubility enhancers (for example, certain small levels of solvents not used as part of the main solvent (examples of which include glycol ethers and glycol ether acetates, valerolactone, ketones, lactones, and the like), and surfactants may be added to the photoresist composition before the solution is coated onto a substrate. Surfactants that improve film thickness uniformity, such as fluorinated surfactants, can be added to the photoresist solution. A sensitizer that transfers energy from a particular range of wavelengths to a different exposure wavelength may also be added to the photoresist composition. Often bases are also added to the photoresist to prevent t-tops or bridging at the surface of the photoresist image. Examples of bases are amines, ammonium hydroxide, and photosensitive bases. Particularly preferred bases are trioctylamine, diethanolamine and tetrabutylammonium hydroxide.

The prepared photoresist composition solution can be applied to a substrate by any conventional method used in the photoresist art, including dipping, spraying, and spin coating. When spin coating, for example, the photoresist solution can be adjusted with respect to the percentage of solids content, in order to provide coating of the desired thickness, given the type of spinning equipment utilized and the amount of time allowed for the spinning process. Suitable substrates include silicon, aluminum, polymeric resins, silicon dioxide, doped silicon dioxide, silicon nitride, tantalum, copper, polysilicon, ceramics, aluminum/copper mixtures; gallium arsenide and other such Group III/V compounds. The photoresist may also be coated over antireflective coatings.

The photoresist coatings produced by the described procedure are particularly suitable for application to silicon/silicon dioxide wafers, such as are utilized in the production of microprocessors and other miniaturized integrated circuit components. An aluminum/aluminum oxide wafer can also be used. The substrate may also comprise various polymeric resins, especially transparent polymers such as polyesters.

The photoresist composition solution is then coated onto the substrate, and the substrate is treated (baked) at a temperature from about 70° C. to about 150° C. for from about 30 seconds to about 180 seconds on a hot plate or for from about 15 to about 90 minutes in a convection oven. This temperature treatment is selected in order to reduce the concentration of residual solvents in the photoresist, while not causing substantial thermal degradation of the solid components. In general, one desires to minimize the concentration of solvents and this first temperature. Treatment (baking) is conducted until substantially all of the solvents have evaporated and a thin coating of photoresist composition, on the order of half a micron (micrometer) in thickness, remains on the substrate. In a preferred embodiment the temperature is from about 95° C. to about 120° C. The treatment is conducted until the rate of change of solvent removal becomes relatively insignificant. The film thickness, temperature and time selection depends on the photoresist properties desired by the user, as well as the equipment used and commercially desired coating times. The coated substrate can then be imagewise exposed to actinic radiation, e.g., ultraviolet radiation, at a wavelength of from about 100 nm (nanometers) to about 300 nm, x-ray, electron beam, ion beam or laser radiation, in any desired pattern, produced by use of suitable masks, negatives, stencils, templates, etc.

The photoresist is then subjected to a post exposure second baking or heat treatment before development. The heating temperatures may range from about 90° C. to about 150° C., more preferably from about 100° C. to about 130° C. The heating may be conducted for from about 30 seconds to about 2 minutes, more preferably from about 60 seconds to about 90 seconds on a hot plate or about 30 to about 45 minutes by convection oven.

The exposed photoresist-coated substrates are developed to remove the image-wise exposed areas by immersion in a developing solution or developed by spray development process. The solution is preferably agitated, for example, by nitrogen burst agitation. The substrates are allowed to remain in the developer until all, or substantially all, of the photoresist coating has dissolved from the exposed areas. Developers include aqueous solutions of ammonium or alkali metal hydroxides. One preferred developer is an aqueous solution of tetramethyl ammonium hydroxide. After removal of the coated wafers from the developing solution, one may conduct an optional post-development heat treatment or bake to increase the coating's adhesion and chemical resistance to etching conditions and other substances. The post-development heat treatment can comprise the oven baking of the coating and substrate below the coating's softening point or UV hardening process. In industrial applications, particularly in the manufacture of microcircuitry units on silicon/silicon dioxide-type substrates, the developed substrates may be treated with a buffered, hydrofluoric acid base etching solution or dry etching. Prior to dry etching the photoresist may be treated to electron beam curing in order to increase the dry-etch resistance of the photoresist.

The invention further provides a method for producing a semiconductor device by producing a photo-image on a substrate by coating a suitable substrate with a photoresist composition. The subject process comprises coating a suitable substrate with a photoresist composition and heat treating the coated substrate until substantially all of the photoresist solvent is removed; image-wise exposing the composition and removing the image-wise exposed areas of such composition with a suitable developer.

The following examples provide illustrations of the methods of producing and utilizing the present invention. These examples are not intended, however, to limit or restrict the scope of the invention in any way and should not be construed as providing conditions, parameters or values which must be utilized exclusively in order to practice the present invention. Unless otherwise specified, all parts and percents are by weight.

EXAMPLE 1

Synthesis of bis[4-acetyloxyphenyl]phenylsulfonium perfluorobutanesulfonate

Bis[4-hydroxylphenyl]phenylsulfonium perfluorobutanesulfonate (10 g) and acetone were placed into a reaction vessel equipped with an agitator, a thermometer, a reflux condenser, and a tube for introducing nitrogen gas into the vessel. Under a nitrogen blanket, 4.6 g of potassium carbonate was added to the reaction vessel and the mixture was stirred for an hour. Acetic anhydride 3.43 gram was added and stirred overnight at room temperature. Dichloromethane (150 ml) and water were added to the reaction vessel and the mixture was stirred for 2 hours. The mixture was then placed into a separatory funnel and the organic (dichloromethane) layer was retained. The dichloromethane layer was washed several times with water, dried over anhydrous sodium sulfate, filtered, and the remaining volatile materials were evaporated to leave an oil. Ether was added to the oil and the mixture was stirred vigorously. A very sticky solid was obtained.

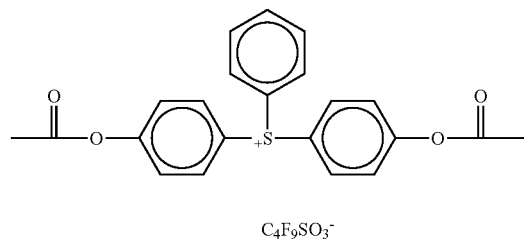

$C_4F_9SO_3^-$

EXAMPLE 2

Synthesis of bis[4-acetyloxyphenyl]phenylsulfonium 4-(1,1,1,2-tetrafluoroethoxy)perfluorobutanesulfonate This material was made following Example 1 except bis[4-hydroxyphenyl]phenysulfonium 4-(1,1,1,2-tetrafluoroethoxy)perfluorobutanesulfonate was used instead of bishydroxylphenylphenysulfonium perfluorobutanesulfonate

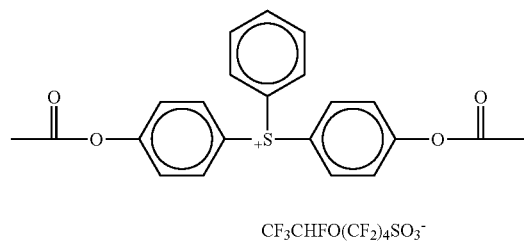

$CF_3CHFO(CF_2)_4SO_3^-$

In addition, the following compounds can be made following the procedure in Example 2 using the corresponding anion:

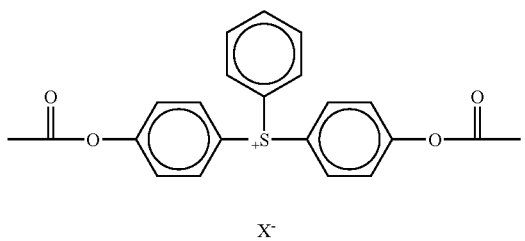

X⁻

Example 2a: Where X=CF$_3$SO3
Example 2b: Where X=N(SO$_2$CF$_3$)$_2$
Example 2c: Where X=N(SO$_2$C$_2$F$_5$)$_2$
Example 2d: Where X=N(SO$_2$CF$_3$)(SO$_2$C$_4$F$_9$)
Example 2e: Where X=N(SO$_2$C$_3$F$_7$)$_2$
Example 2f: Where X=C(SO$_2$CF$_3$)$_3$
Example 2g: Where X=CH$_3$CH$_3$CH$_3$O(CF$_2$)$_4$SO$_3$
Example 2h: Where X=C$_4$F$_9$SO$_3$

EXAMPLE 3

Synthesis of bis[2-methyladamantylacetyloxymethoxyphenyl]phenylsulfonium perfluorobutanesulfonate This material was made following the procedure in Example 1 except 2-methyladamantylbromoacetate was used in place of acetic anhydride.

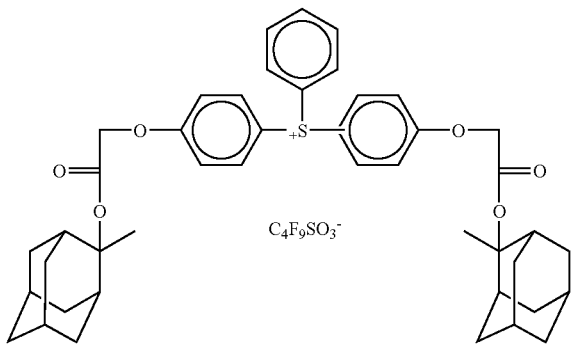

C$_4$F$_9$SO$_3$⁻

In addition, the following compounds can be made following the procedure in Example 3 using the corresponding anion:

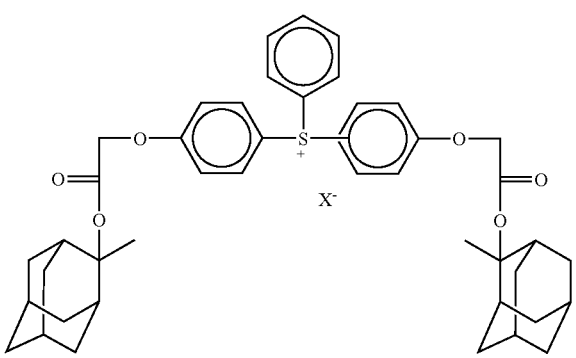

X⁻

Example 3a: Where X=CF$_3$CHFO(CF$_2$)$_4$SO$_3$
Example 3b: Where X=CF$_3$SO$_3$ Example 3c: Where X=N(SO$_2$CF$_3$)$_2$
Example 3d: Where X=N(SO$_2$C$_2$F$_5$)$_2$
Example 3e: Where X=N(SO$_2$CF$_3$)(SO$_2$C$_4$F$_9$)
Example 3f: Where X=N(SO$_2$C$_3$F$_7$)$_2$
Example 3g: Where X=CH$_3$CH$_3$CH$_3$O(CF$_2$)$_4$SO$_3$
Example 3h: Where X=C(SO$_2$CF$_3$)$_3$
Example 3i: Where X=C$_4$F$_9$SO$_3$

EXAMPLE 4

Synthesis of bis[4,4-bis(trifluoromethyl)-3-oxatricyclo[4.2.1.0$^{2,5}$]-nonylmethoxyphenyl]phenyl sulfonium perfluorobutanesulfonate Bis hydroxylphenylphenysulfonium perfluorobutanesulfonate (10 g) and acetone were placed into a reaction vessel equipped with an agitator, a thermometer, a reflux condenser, and a tube for introducing nitrogen gas into the vessel. Under a nitrogen blanket, 4.6 g of potassium carbonate was added to the reaction vessel and the mixture was stirred for an hour. 4,4-bis(trifluoromethyl)-3-oxatricyclo[4.2.1.0$^{2,5}$]nonyl chloromethylether (10.92 g) was added to the reaction mixture and the mixture was stirred overnight at room temperature. Dichloromethane (150 ml) and water were added to the reaction vessel and the mixture was stirred for 2 hours. The mixture was then placed into a separatory funnel and the organic (dichloromethane) layer was retained. The dichloromethane layer was washed several times with water, dried over anhydrous sodium sulfate, filtered, and the remaining volatile materials were evaporated to leave an oil. Ether was added to the oil and the mixture was stirred vigorously. A very sticky solid was obtained.

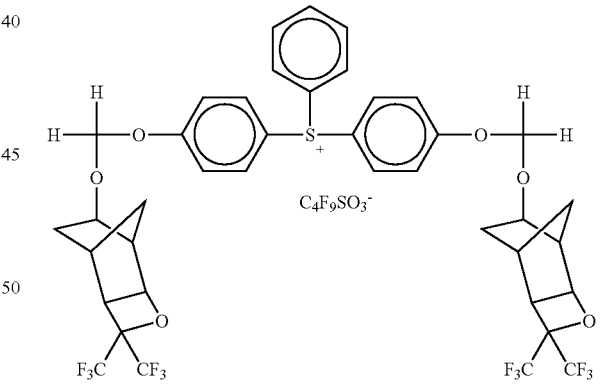

C$_4$F$_9$SO$_3$⁻

EXAMPLE 4a

Synthesis of bis[4,4-bis(trifluoromethyl)-3-oxatricyclo[4.2.1.0$^{2,5}$]-nonylmethoxyphenyl]phenyl sulfonium perfluoromethanesulfonate This can be made from bis hydroxylphenylphenysulfonium perfluoromethanesulfonate and 4,4-bis(trifluoromethyl)-3-oxatricyclo[4.2.1.0$^{2,5}$]nonyl chloromethylether following the procedure in Example 4.

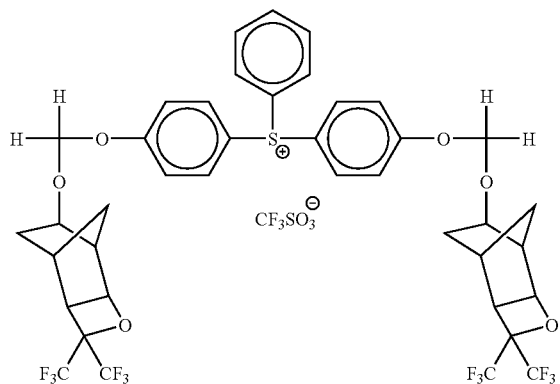

EXAMPLE 4b

Synthesis of bis[4,4-bis(trifluoromethyl)-3-oxatricyclo[4.2.1.0$^{2,5}$]-nonylmethoxyphenyl]phenyl sulfonium 4-(1,1,1,2-tetrafluoroethoxy)perfluorobutyl sulfonate This can be made from bis[4,4-bis(trifluoromethyl)-3-oxatricyclo-[4.2.1.0$^{2,5}$]nonyl-methoxyphenyl]phenyl sulfonium perfluoromethanesulfonate and 4-(1,1,1,2-tetrafluoroethoxy)perfluorobutanesulfonic acid lithium salt following the procedure in Example 4.

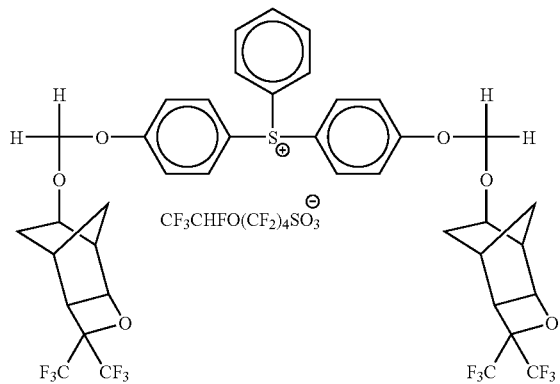

EXAMPLE 4c

Synthesis of bis[4,4-bis(trifluoromethyl)-3-oxatricyclo[4.2.1.0$^{2,5}$]-nonylmethoxyphenyl]phenyl sulfonium bis(trifluoromethylsulfonyl)imide This can be made from bis[4,4-bis(trifluoromethyl)-3-oxatricyclo-[4.2.1.0$^{2,5}$]nonyl-methoxyphenyl]phenyl sulfonium perfluoromethanesulfonate and bisperfluoromethane sulfonimide acid by following the procedure in Example 4.

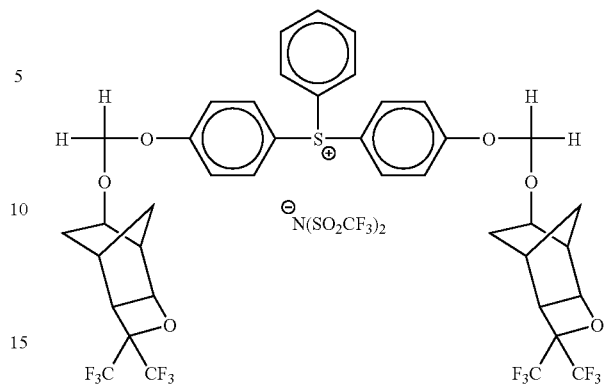

In addition, the following compounds can be made following the procedure in Example 4 using the corresponding anion:

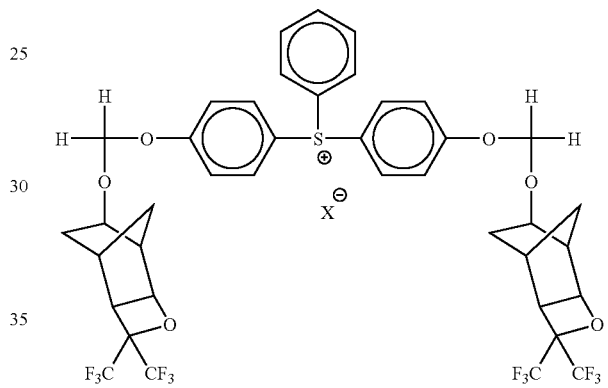

Example 4d: Where X=N(SO$_2$C$_2$F$_5$)$_2$
Example 4e: Where X=N(SO$_2$CF$_3$)(SO$_2$C$_4$F$_9$)
Example 4f: Where X=N(SO$_2$C$_3$F$_7$)$_2$
Example 4g: Where X=N(SO$_2$C$_4$F$_9$)$_2$
Example 4h: Where X=C(SO$_2$CF$_3$)$_3$
Example 4i: Where X=CH$_3$CH$_3$CH$_3$O(CF$_2$)$_4$SO$_3$

EXAMPLE 5

Synthesis of bis[4-hydroxyphenyl]phenylsulfonium bis(perfluoroethylsulfonyl)imide Bis[4-hydroxylphenyl]phenysulfonium perfluoromethanesulfonate (15.0 g) and an acetone-water mixture were placed into a reaction vessel equipped with an agitator, a thermometer, a reflux condenser, and a tube for introducing nitrogen gas into the vessel. Under a nitrogen blanket, 9.6 g lithium bisperfluoroethane sulfonimide was added to the reaction vessel and the mixture was stirred for 5 hours. Dichloromethane (150 ml) and water were added to the reaction vessel and the mixture was stirred for 2 hours. The mixture was then placed into a separatory funnel and the organic (dichloromethane) layer was retained. The dichloromethane layer was washed several times with water, dried over anhydrous sodium sulfate, filtered, and the remaining volatile materials were evaporated to leave an oil. Ether was added to the oil and the mixture was stirred vigorously. An oil was obtained.

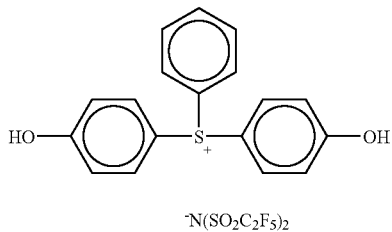

In addition, the following, the following compounds can be made as in Example 5 using the corresponding anion:

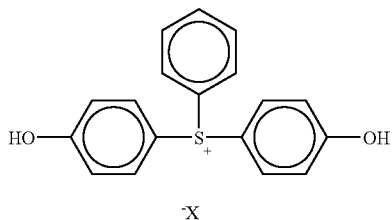

Example 5a: Where X=N(SO$_2$CF$_3$)$_2$
Example 5b: Where X=N(SO$_2$CF3)(SO$_2$C$_4$F$_9$)

Example 5c: Where X=N(SO$_2$C$_3$F$_7$)$_2$
Example 5d: Where X=N(SO$_2$C$_4$F$_9$)$_2$
Example 5e: Where X=C(SO$_2$CF$_3$)$_3$
Example 5f: Where X=CF$_3$CHFO(CF$_2$)$_4$SO$_3$
Example 5g Where X=CH$_3$CH$_3$CH$_3$O(CF$_2$)$_4$SO$_3$
Example 5h Where X=C$_4$F$_9$SO$_3$
Example 5i Where X=CF$_3$SO$_3$

EXAMPLE 6

Synthesis of bis[4-pentafluorobenzenesulfonyloxyphenyl]phenylsulfonium bis(perfluoroethylsulfonyl)imide Bis[4-hydroxyphenyl]phenylsulfonium bis(perfluoroethylsulfonyl)imide (6.33 g) from Example 5 and dry THF were placed into a reaction vessel equipped with an agitator, a thermometer, a reflux condenser, and a tube for introducing nitrogen gas into the vessel. A dry ice-acetone bath was placed around the reaction vessel and under a nitrogen blanket, 5.09 g of pentafluorobenzene sulfonyl chloride was added to the reaction vessel and the mixture was stirred for 5 hours. Dichloromethane (150 ml) and water were added to the reaction vessel and the mixture was stirred for 2 hours. The mixture was then placed into a separatory funnel and the organic (dichloromethane) layer was retained. The dichloromethane layer was washed several times with water, dried over anhydrous sodium sulfate, filtered, and the remaining volatile materials were evaporated to leave an oil. Ether was added to the oil and the mixture was stirred vigorously. White crystals, mp 38° C., were recovered.

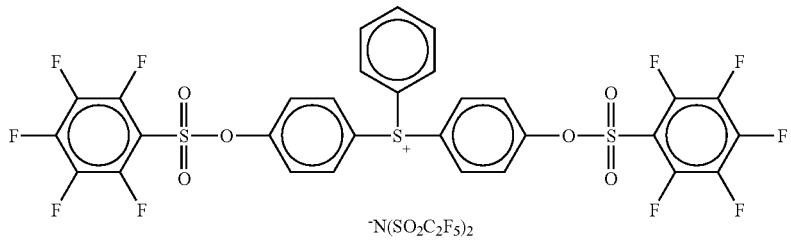

In addition, the following, the following compounds can be made as in Example 6 using the corresponding anion:

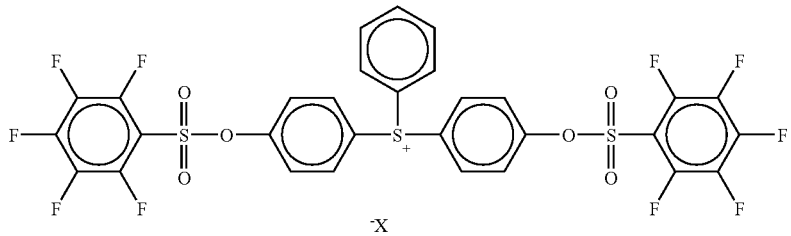

Example 6a: Where X=N(SO$_2$CF$_3$)$_2$
Example 6b: Where X=N(SO$_2$CF$_3$)(SO$_2$C$_4$F$_9$)
Example 6c: Where X=N(SO$_2$C$_3$F$_7$)$_2$
Example 6d: Where X=N(SO$_2$C$_4$F$_9$)$_2$
Example 6e Where X=C(SO$_2$CF$_3$)$_3$
Example 6f: Where X=CF$_3$CHFO(CF$_2$)$_4$SO$_3$
Example 6g: Where X=CH$_3$CH$_3$CH$_3$O(CF$_2$)$_4$SO$_3$
Example 6h Where X=C$_4$F$_9$SO$_3$
Example 6i Where X=CF$_3$SO$_3$

EXAMPLE 7

Synthesis of bis[4-(3,5-di(trifluoromethyl)benzene-sulfonyloxy)phenyl]phenylsulfonium bis(perfluoro-ethylsulfonyl)imide This can be made by using 3,5-di(trifluoromethyl)benzene sulfonyl chloride instead of pentafluorobenzene sulfonyl chloride and following the procedure in Example 6.

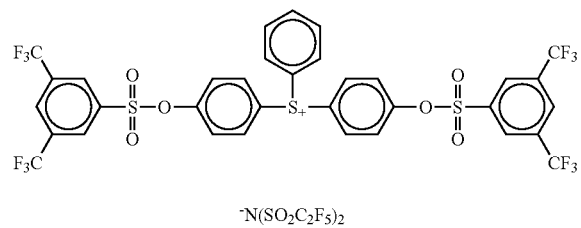

$^-N(SO_2C_2F_5)_2$

In addition, the following, the following compounds can be made as in Example 7 using the corresponding anion:

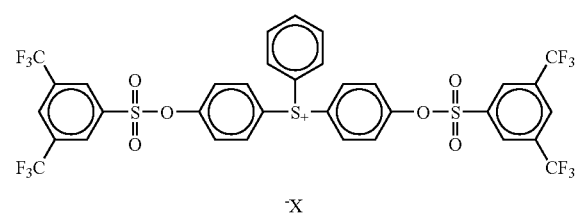

X

Example 7a: Where X=$N(SO_2CF_3)_2$
Example 7b: Where X=$N(SO_2CF_3)(SO_2C_4F_9)$
Example 7c: Where X=$N(SO_2C_3F_7)_2$
Example 7d: Where X=$N(SO_2C_4F_9)_2$
Example 7e Where X=$C(SO_2CF_3)_3$
Example 7f: Where X=$CF_3CHFO(CF_2)_4SO_3$
Example 7g: Where X=$CH_3CH_3CH_3O(CF_2)_4SO_3$
Example 7h Where X=$C_4F_9SO_3$
Example 7i Where X=$CF_3SO_3$

EXAMPLE 8

Synthesis of bis[4-trifluoromethylsulfonylox-yphenyl]phenylsulfonium bis(perfluoroethylsulfo-nyl)imide This can be made by using trifluoromethyl sulfonyl chloride instead of pentafluorobenzene sulfonyl chloride and following the procedure in Example 6.

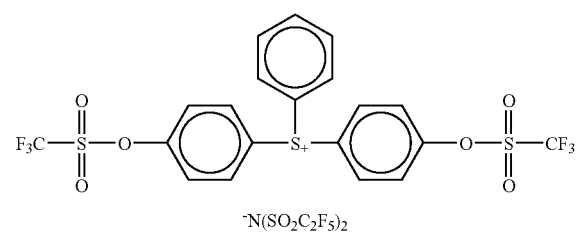

$^-N(SO_2C_2F_5)_2$

In addition, the following, the following compounds can be made as in Example 8 using the corresponding anion:

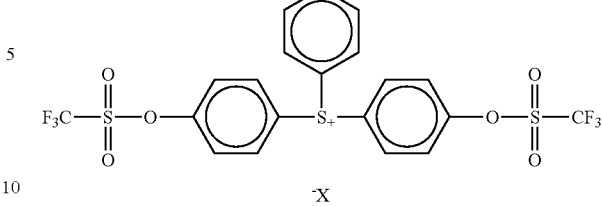

X

Example 8a: Where X=$N(SO_2CF_3)_2$
Example 8b: Where X=$N(SO_2CF_3)(SO_2C_4F_9)$
Example 8c: Where X=$N(SO_2C_3F_7)_2$
Example 8d: Where X=$N(SO_2C_4F_9)_2$
Example 8e Where X=$C(SO_2CF_3)_3$
Example 8f: Where X=$CF_3CHFO(CF_2)_4SO_3$
Example 8g: Where X=$CH_3CH_3CH_3O(CF_2)_4SO_3$
Example 8h Where X=$C_4F_9SO_3$
Example 8i Where X=$CF_3SO_3$

EXAMPLE 9

2.1625 g of poly(EAdMA/MAdMA/HAdMA/α-GBLMA; 20/20/25/35) polymer, 0.0504 g (30 µmol/g) of bis[acetyloxyphenyl]phenylsulfonium trifluoroethoxyper-fluorobutanesulfonate from Example 2, 0.23 g of DIPA 10 weight % in PGMEA) and 0.0360 g of 10 weight % PGMEA solution of a surfactant (fluoroaliphatic polymeric ester, supplied by 3M Corporation, St. Paul Minn.) were dissolved in 27.74 g of AZ Thinner and passed through a 0.2 µm filter to give a 30 g photoresist solution.

EXAMPLE 10

A silicon substrate coated with a bottom antireflective coating (B.A.R.C.) was prepared by spin coating the bottom antireflective coating solution (AZ® EXP ArF-1, B.A.R.C. available from AZ Electronic Materials USA Corp., Somerville, N.J.) onto the silicon substrate and baking at 215° C. for 60 sec. The B.A.R.C film thickness was 29 nm. The photoresist solution from Example 9 was then coated on the B.A.R.C coated silicon substrate. The spin speed was adjusted such that the photoresist film thickness was thickness 180 nm, Nikon 306D 0.85NA & 4/5 Annular Illumination, PAB100° C./60 s, PEB 110° C./60 s, Development time: 30 s (ACT12), 6% PSM. The imaged photoresist was then developed using a 2.38 weight % aqueous solution of tetramethyl ammonium hydroxide for 30 sec. The line and space patterns were then observed on a scanning electron microscope. The photoresist had a photosensitivity of 47.6 mJ/cm², had very good exposure latitude (16.8%), good LER and profile shape.

EXAMPLE 11

Example 9 was repeated using bis[2-methyladamanty-lacetyloxymethoxyphenyl]phenylsulfonium perfluorobu-tanesulfonate from Example 3 instead of bis[acetyloxyphe-nyl]phenylsulfonium trifluoroethoxyperfluorobutanesulfonate.

EXAMPLE 12

Example 10 was repeated with photoresist solution from Example 11 and similar results were obtained.

EXAMPLE 13

Example 9 was repeated using bis[4,4-bis(trifluoromethyl)-3-oxatricyclo-[4.2.1.0$^{2,5}$]nonylmethoxyphenyl]phenyl sulfonium perfluorobutanesulfonate from Example 4 instead of bis[acetyloxyphenyl]phenylsulfonium trifluoroethoxyperfluorobutanesulfonate.

EXAMPLE 14

Example 10 was repeated with photoresist solution from Example 13 and similar results were obtained.

EXAMPLE 15

Example 9 was repeated using [4-hydroxyphenyl]phenylsulfonium bis(perfluoroethylsulfonyl)imide from Example 5 instead of bis[acetyloxyphenyl]phenylsulfonium trifluoroethoxyperfluorobutanesulfonate.

EXAMPLE 16

Example 10 was repeated with photoresist solution from Example 15 and similar results were obtained.

EXAMPLE 17

Example 9 was repeated using [4-pentafluorobenzenesulfonyloxyphenyl]phenylsulfonium bis(perfluoroethylsulfonyl)imide from Example 6 instead of bis[acetyloxypherlyl]phenylsulfonium trifluoroethoxyperfluorobutanesulfonate.

EXAMPLE 18

Example 10 was repeated with photoresist solution from Example 17 and similar results were obtained.

EXAMPLE 19

2.1625 g of poly(EAdMA/HAdA/NLA/AdMA; 30/20/40/10) polymer, 0.0504 g (30 μmol/g) of bis[acetyloxyphenyl]phenylsulfonium trifluoroethoxyperfluorobutanesulfonate from Example 2, 0.23 g of DIPA 10 weight % in PGMEA) and 0.0360 g of 10 weight % PGMEA solution of a surfactant (fluoroaliphatic polymeric ester, supplied by 3M Corporation, St. Paul Minn.) were dissolved in 27.74 g of AZ Thinner and passed through a 0.2 μm filter to give a 30 g photoresist solution.

EXAMPLE 20

A silicon substrate coated with a bottom antireflective coating (B.A.R.C.) was prepared by spin coating the bottom antireflective coating solution (AZ® EXP ArF-1, B.A.R.C. available from AZ Electronic Materials USA Corp., Somerville, N.J.) onto the silicon substrate and baking at 215° C. for 60 sec. The B.A.R.C film thickness was 29 nm. The photoresist solution from Example 19 was then coated on the B.A.R.C coated silicon substrate. The spin speed was adjusted such that the photoresist film thickness was thickness 180 nm, Nikon 306D 0.85NA & 4/5 Annular Illumination, PAB100° C./60 s, PEB 110° C./60 s, Development time: 30 s (ACT12), 6% PSM. The imaged photoresist was then developed using a 2.38 weight % aqueous solution of tetramethyl ammonium hydroxide for 30 sec. The line and space patterns were then observed on a scanning electron microscope. The photoresist had a photosensitivity of 55.5 mJ/cm$^2$, had very good exposure latitude (16.8%), good LER and profile shape.

EXAMPLE 21

2.1625 g of poly(EAdMA/HAdA/NLA/AdA; 30/20/40/10) polymer, 0.0504 g (30 μmol/g) of bis[acetyloxyphenyl]phenylsulfonium trifluoroethoxyperfluorobutanesulfonate from Example 2, 0.23 g of DIPA 10 weight % in PGMEA) and 0.0360 g of 10 weight % PGMEA solution of a surfactant (fluoroaliphatic polymeric ester, supplied by 3M Corporation, St. Paul Minn.) were dissolved in 27.74 g of AZ Thinner and passed through a 0.2 μm filter to give a 30 g photoresist solution.

EXAMPLE 22

A silicon substrate coated with a bottom antireflective coating (B.A.R.C.) was prepared by spin coating the bottom antireflective coating solution (AZ® EXP ArF-1, B.A.R.C. available from AZ Electronic Materials USA Corp., Somerville, N.J.) onto the silicon substrate and baking at 215° C. for 60 sec. The B.A.R.C film thickness was 29 nm. The photoresist solution from Example 21 was then coated on the B.A.R.C coated silicon substrate. The spin speed was adjusted such that the photoresist film thickness was thickness 180 nm, Nikon 306D 0.85NA & 4/5 Annular Illumination, PAB100° C./60 s, PEB 110° C./60 s, Development time: 30 s (ACT12), 6% PSM. The imaged photoresist was then developed using a 2.38 weight % aqueous solution of tetramethyl ammonium hydroxide for 30 sec. The line and space patterns were then observed on a scanning electron microscope. The photoresist had a photosensitivity of 44.5 mJ/cm$^2$, had very good exposure latitude (16.0%), good LER and profile shape.

EXAMPLE 23

Examples 9, 11, 13, 15, and 17 can be repeated by substituting the polymer therein with one of the following polymers:
poly(2-ethyl-2-adamantyl methacrylate-co-3-hydroxy-1-adamantyl acrylate-co-α-gamma-butyrolactone acrylate-co-tricyclo[5,2,1,02,6]deca-8-yl methacrylate); poly(2-ethyl-2-adamantyl methacrylate-co-3-hydroxy-1-adamantyl acrylate-co-β-gamma-butyrolactone methacrylate); poly(2-ethyl-2-adamantyl methacrylate-co-3-hydroxy-1-adamantyl acrylate-co-α-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-β-gamma-butyrolactone methacrylate-co-tricyclo[5,2,1,0$^{2,6}$]deca-8-yl methacrylate); poly(2-ethyl-2-adamantyl methacrylate-co-3-hydroxy-1-adamantyl acrylate-co-isobutyl methacrylate-co-α-gamma-butyrolactone acrylate); poly(2-ethyl-2-adamantyl methacrylate-co-3-hydroxy-1-adamantyl acrylate-co-α-gamma-butyrolactone acrylate); poly(2-ethyl-2-adamantyl methacrylate-co-3-hydroxy-1-adamantyl acrylate-co-β-gamma-butyrolactone acrylate); poly(2-ethyl-2-adamantyl methacrylate-co-3-hydroxy-1-adamantyl acrylate-co-tricyclo[5,2,1,02,6]deca-8-yl methacrylate-co-α-gamma-butyrolactone methacrylate); poly(2-ethyl-2-adamantyl methacrylate-co-3-hydroxy-1-adamantyl acrylate-co-α-gamma-butyrolactone methacrylate-co-2-adamantyl methacrylate); poly(2-ethyl-2-adamantyl methacrylate-co-3-hydroxy-1-adamantyl acrylate-co-α-gamma-butyrolactone methacrylate); poly (2-ethyl-2-adamantyl methacrylate-co-3-hydroxy-1- methacryloxyadamantane-co-β-gamma-butyrolactone methacrylate); poly(2-methyl-2-adamantyl acrylate-co-3-hydroxy-1-methacryloxyadamantane-co-α-gamma-butyrolactone methacrylate); poly(2-methyl-2-adamantyl methacrylate-co-2-ethyl-2-adamantyl methacrylate-co-3-hydroxy-1-methacryloxyadamantane-co-α-gamma-butyrolactone methacrylate); poly(2-methyl-2-adamantyl methacrylate-co-2-ethyl-2-adamantyl methacrylate-co-β-gamma-butyrolactone methacrylate-co-3-hydroxy-1-methacryloxyadamantane); poly(2-methyl-2-adamantyl methacrylate-co-2-ethyl-2-adamantyl methacrylate-co-α-gamma-butyrolactone methacrylate-co-3-hydroxy-1-methacryloxyadamantane); poly(2-methyl-2-adamantyl methacrylate-co-3,5-dihydroxy-1-methacryloxyadamantane-co-α-gamma-butyrolactone methacrylate); poly(2-methyl-2-adamantyl methacrylate-co-3,5-dimethyl-7-hydroxy adamantyl methacrylate-co-α-gamma-butyrolactone methacrylate); poly(2-methyl-2-adamantyl methacrylate-co-3-hydroxy-1-adamantyl acrylate-co-α-gamma-butyrolactone methacrylate); poly(2-methyl-2-adamantyl methacrylate-co-3-hydroxy-1-methacryloxyadamantane-co-β-gamma-butyrolactone methacrylate); poly(2-methyl-2-adamantyl methacrylate-co-3-hydroxy-1-methacryloxyadamantane-co-α-gamma-butyrolactone methacrylate-co-tricyclo[5,2,1,0$^{2,6}$]deca-8-yl methacrylate); poly(2-methyl-2-adamantyl methacrylate-co-3-hydroxy-1-methacryloxyadamantane-co-β-gamma-butyrolactone methacrylate-co-tricyclo[5,2,1,0$^{2,6}$]deca-8-yl methacrylate); poly(2-methyl-2-adamantyl methacrylate-co-3-hydroxy-1-methacryloxyadamantane-co-α-gamma-butyrolactone methacrylate-co-2-ethyl-2-adamantyl methacrylate); poly(2-methyl-2-adamantyl methacrylate-co-3-hydroxy-1-methacryloxyadamantane-co-α-gamma-butyrolactone methacrylate-co-2-ethyl-2-adamantyl-co-methacrylate); poly(2-methyl-2-adamantyl methacrylate-co-methacryloyloxy norbornene methacrylate-co-β-gamma-butyrolactone methacrylate); poly(2-methyl-2-adamantyl methacrylate-co-methacryloyloxy norbornene methacrylate-co-β-gamma-butyrolactone methacrylate-co-2-adamantyl methacrylate-co-3-hydroxy-1-methacryloxyadamantane); poly(2-methyl-2-adamantyl methacrylate-co-methacryloyloxy norbornene methacrylate-co-tricyclo[5,2,1,02,6]deca-8-yl methacrylate-co-3-hydroxy-1-methacryloxyadamantane-co-α-gamma-butyrolactone methacrylate); poly(2-methyl-2-adamantyl methacrylate-co-β gamma-butyrolactone methacrylate-co-2-adamantyl methacrylate-co-3-hydroxy-1-methacryloxyadamantane); poly(2-methyl-2-adamantyl methacrylate-co-β-gamma-butyrolactone methacrylate-co-3-hydroxy-1-methacryloxyadamantane-co-ethylcyclopentylacrylate); poly(2-methyl-2-adamantyl methacrylate-co-β-gamma-butyrolactone methacrylate-co-3-hydroxy-1-adamantyl acrylate-co-tricyclo[5,2,1,02,6]deca-8-yl methacrylate); poly(ethylcyclopentylmethacrylate-co-2-ethyl-2-adamantyl methacrylate-co-α-gamma-butyrolactone acrylate); and poly(t-butyl norbornene carboxylate-co-maleic anhydride-co-2-methyl-2-adamantyl methacrylate-co-β-gamma-butyrolactone methacrylate-co-methacryloyloxy norbornene methacrylate)
to form a photoresist solution. The photoresist solution can be tested as in Example 10 and the photoresists are expected to have good properties.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The invention claimed is:

1. A compound selected from bis[4,4-bis(trifluoromethyl)-3-oxatricyclo[4.2.1.0$^{2,5}$]nonyl-methoxyphenyl]phenyl sulfonium bis(trifluoromethylsulfonyl)imide, bis[4,4-bis(trifluoromethyl)-3-oxatricyclo-[4.2.1.0$^{2,5}$]-nonylmethoxyphenyl]phenyl sulfonium bis (perfluoroethylsulfonyl)-imide, bis[4,4-bis(trifluoromethyl)-3-oxatricyclo[4.2.1.0$^{2,5}$]-nonylmethoxyphenyl]phenyl sulfonium (perfluoromethyl-sulfonyl)(perfluorobutylsulfonyl)imide, bis[4,4-bis(trifluoromethyl)-3-oxatricyclo [4.2.1.0$^{2,5}$]-nonylmethoxyphenyl]phenyl sulfonium bis(perfluoropropyl-sulfonyl)imide, bis[4,4-bis(trifluoromethyl)-3-oxatricyclo[4.2.1.0$^{2,5}$]nonylmethoxyphenyl]phenyl sulfonium bis(perfluorobutylsulfonyl)imide, bis[4,4-bis(trifluoromethyl)-3-oxatricyclo-[4.2.1.0$^{2,5}$]-nonylmethoxyphenyl]phenyl sulfonium tris(trifluoromethyl-sulfonyl)methide, bis[2-methyladamantylacetyloxymethoxyphenyl]phenylsulfonium bis(trifluoromethylsulfonyl)imide, bis[2-methyladamantylacetyloxy-methoxy-phenyl]phenylsulfonium bis(perfluoroethylsulfonyl)imide, bis[2-methyladamantyl-acetyloxymethoxyphenyl]phenylsulfonium (perfluoromethyl-sulfonyl) (perfluorobutylsulfonyl)imide, bis[2-methyladamantyl-acetyloxymethoxy-phenyl]phenylsulfonium bis(perfluoropropylsulfonyl)imide, bis[2-methyladamantylacetyloxy-methoxyphenyl]phenylsulfonium tris (trifluoromethyl-sulfonyl)methide, bis[2-methyladamantylacetyloxymethoxyphenyl] phenylsulfonium bis(perfluorobutylsulfonyl)imide, bis[4-pentafluorobenzene-sulfonyloxyphenyl]phenylsulfonium bis(perfluoroethylsulfonyl)imide, bis[4-pentafluorobenzene-sulfonyloxyphenyl]phenylsulfonium bis(trifluoromethyl-sulfonyl)imide, bis[4-pentafluorobenzene-sulfonyloxyphenyl]phenylsulfonium (perfluoromethylsulfonyl) (perfluorobutyl-sulfonyl)imide, bis[4-pentafluoro-benzenesulfonyloxyphenyl]phenylsulfonium bis (perfluoropropylsulfonyl)imide, bis[4-pentafluorobenzenesulfonyloxyphenyl]phenylsulfonium bis (perfluorobutyl-sulfonyl)imide, bis[4-pentafluorobenzenesulfonyl-oxyphenyl]phenylsulfonium tris(trifluoromethylsulfonyl)methide, bis[4-(3,5-di(trifluoromethyl)-benzenesulfonyloxy)phenyl]phenylsulfonium bis (perfluoroethylsulfonyl)imide, bis[4-(3,5-di(trifluoromethyl)benzenesulfonyloxy)-phenyl]phenylsulfonium bis (trifluoromethylsulfonyl)imide, bis[4-(3,5-di(trifluoromethyl)benzene-sulfonyloxy)phenyl]phenylsulfonium (perfluoromethylsulfonyl)(perfluorobutylsulfonyl)imide, bis [4-(3,5-di(trifluoromethyl)benzenesulfonyl-oxy)phenyl] phenylsulfonium bis(perfluoropropylsulfonyl)imide, bis[4-(3,5-di(trifluoromethyl)benzenesulfonyloxy)phenyl] phenylsulfonium bis(perfluorobutylsulfonyl)imide, bis[4-(3,5-di(trifluoromethyl)benzenesulfonyloxy)phenyl] phenylsulfonium tris(trifluoromethylsulfonyl)methide, bis [4-trifluoromethylsulfonyloxy)phenyl]phenylsulfonium bis (perfluoro-ethyl-sulfonyl)imide, bis[4- trifluoromethylsulfonyloxy)phenyl]phenylsulfonium bis(trifluoromethyl-sulfonyl)imide, bis[4-trifluoromethylsulfonyloxy)phenyl]phenylsulfonium (perfluoromethylsulfonyl)(perfluorobutylsulfonyl)imide, bis[4-trifluoromethylsulfonyloxy)phenyl]phenylsulfonium bis(perfluoropropyl-sulfonyl)imide, bis[4-trifluoromethylsulfonyloxy)phenyl]phenylsulfonium bis(perfluorobutylsulfonyl)imide, and bis[4-trifluoromethylsulfonyloxy)phenyl]phenylsulfonium tris(trifluoromethylsulfonyl)methide.

2. A photoresist composition useful for imaging in deep UV comprising:
 a) a polymer containing an acid labile group; and,
 b) a compound of claim 1.

3. The composition of claim 2 which further comprises another photoacid generator.

4. A process for imaging a photoresist comprising the steps of:
 a) coating a substrate with the composition of claim 2;
 b) baking the substrate to substantially remove the solvent;
 c) image-wise exposing the photoresist coating;
 d) postexposure baking the photoresist coating; and
 e) developing the photoresist coating with an aqueous alkaline solution.

5. The process of claim 4, where the image-wise exposure wavelength is below 300 nm.

6. The process according to claim 4, where the substrate is selected from a microelectronic device and a liquid crystal display substrate.

7. A compound selected from bis [4-acetyloxyphenyl]phenyl sulfonium 4-(1,1,1,2-tetrafluoroethoxy)perfluorobutanesulfonate, bis[2-methyladamantyl-acetyloxymethoxyphenyl]phenylsulfonium perfluoro-butanesulfonate, bis[4,4-bis(trifluoromethyl)-3-oxatricyclo[4.2.1.0$^{2,5}$]nonyl-methoxyphenyl]phenyl sulfonium perfluorobutanesulfonate, bis [4,4-bis(trifluoromethyl)-3-oxatricyclo[4.2.1.0$^{2,5}$]-nonylmethoxyphenyl]phenyl sulfonium perfluoromethanesulfonate, bis [4,4-bis(trifluoromethyl)-3-oxatrioyclo[4.2.1.0$^{2,5}$]-nonylmethoxyphenyl]phenyl sulfonium 4-(1,1,1,2-tetrafluoroethoxy)perfluoro-butanesulfonate, bis[4-acetyloxyphenyl]phenylsulfonium 4-propoxyperfluorobutanesulfonate, bis[2-methyladamantylacetyl-oxymethoxyphenyl]phenylsulfonium 4-(1,1,1,2-tetrafluoroethoxy)perfluorobutane-sulfonate, bis [2-methyladamantylacetyl-oxymethoxyphenyl]phenylsulfonium perfluoromethanesulfonate, bis [2-methytadamantyl-acetyl-oxymethoxyphenyl]phenylsulfonium 4-propoxyperfluorobutanesulfonate, bis [4,4-bis(trifluoromethyl)-3-oxatricyclo-[4.2.1.0$^{2,5}$]nonylmethoxyphenyl]phenyl sulfonium 4-propoxyperfluorobutanesulfonate, and bis [4-hydroxyphenyl]-phenylsulfonium 4-(1,1,1,2-tetrafluoroethoxy)perfluorobutanesulfonate, bis [4-hydroxyphenyl]-phenylsulfonium 4-propoxyperfluorobutanesulfonate.

8. A photoresist composition useful for imaging in deep UV comprising:
 a) a polymer containing an acid labile group; and,
 b) a compound of claim 7.

9. The composition of claim 8 which further comprises another photoacid generator.

* * * * *